United States Patent
Guicquero et al.

[11] Patent Number: 5,879,445
[45] Date of Patent: *Mar. 9, 1999

[54] THINNERS FOR AQUEOUS SUSPENSIONS OF MINERAL PARTICLES AND HYDRAULIC BINDER PASTES

[75] Inventors: Jean-Pierre Guicquero, Santeny; Martin Mosquet, Pithiviers; Yves Chevalier, Irigny; Pierre Le Perchec, Lyons, all of France

[73] Assignee: Chryso (S.A.), Montrouge, France

[ * ] Notice: This patent issued on a continued prosecution application filed under 37 CFR 1.53(d), and is subject to the twenty year patent term provisions of 35 U.S.C. 154(a)(2).

[21] Appl. No.: 411,598

[22] PCT Filed: Oct. 11, 1993

[86] PCT No.: PCT/FR93/01004

§ 371 Date: Jun. 29, 1995

§ 102(e) Date: Jun. 29, 1995

[87] PCT Pub. No.: WO94/08913

PCT Pub. Date: Apr. 28, 1994

[30] Foreign Application Priority Data

Oct. 12, 1992 [FR] France .................. 92 12496

[51] Int. Cl.⁶ .................. C04B 24/12
[52] U.S. Cl. .................. 106/696; 106/724; 106/727; 106/808; 106/823; 524/220; 524/221; 524/368; 524/650
[58] Field of Search .................. 106/696, 724, 106/727, 808, 823; 524/220, 221, 368, 650

[56] References Cited

U.S. PATENT DOCUMENTS

| 3,210,410 | 10/1965 | Gaertner .................. 106/808 |
| 3,615,779 | 10/1971 | Von Freyhold . |
| 3,718,603 | 2/1973 | Mitchell .................. 210/58 |
| 3,976,589 | 8/1976 | Mitchell .................. 252/180 |
| 4,518,725 | 5/1985 | Guicquero . |
| 4,797,459 | 1/1989 | Cuscurida et al. .................. 524/368 |
| 5,069,798 | 12/1991 | Hwa et al. .................. 210/700 |
| 5,100,984 | 3/1992 | Bürge et al. . |
| 5,336,316 | 8/1994 | Dawson et al. .................. 106/724 |
| 5,338,477 | 8/1994 | Chen et al. .................. 252/180 |

FOREIGN PATENT DOCUMENTS

| 0118316 | 12/1984 | European Pat. Off. . |
| 2 704 853 | 11/1994 | France . |
| WO 95/166430 | 6/1995 | WIPO . |

OTHER PUBLICATIONS

Hawley's Condensed Chemical Dictionary, p. 1148, Van Norstrand Reinhold (no date available).

Comprehensive Dictionary of Engineering and Technology, vol. X English–French, pp. 1254, 1255 (no date available).

*Primary Examiner*—Paul Marcantoni
*Attorney, Agent, or Firm*—Cummings & Lockwood

[57] ABSTRACT

A process for fluidizing an aqueous suspension of mineral particles or hydraulic binder pastes which comprises admixing said aqueous suspension of mineral particles or hydraulic binder pastes with one or more compounds or salts of compounds corresponding to the general formula:

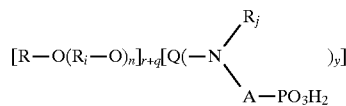

wherein:

R is a hydrogen atom or a saturated or unsaturated monovalent hydrocarbon group comprising 1 to 18 carbon atoms and optionally one or more heteroatoms;

$R_i$ is an alkylene or an arylene group optionally comprising one or more heteroatoms;

Q is a hydrocarbon group comprising 2 to 18 carbon atoms and optionally one or more heteroatoms;

A is an alkylidene group comprising 1 to 5 carbon atoms;

$R_j$ is selected from the group consisting of an $A-PO_3H_2$ group, an alkyl group comprising 1 to 18 carbon atoms and the group wherein $R_k$ is selected from the group consisting of an $A-PO_3H_2$ group and an alkyl group and B is an alkylene group;

n is 1 to 10,000;

r is the sum of $[R-O(R_i-O)_n]$ groups carried by all the $R_j$ groups;

q is the number of $[R-O(R_i-O)_n]$ groups carried by Q;

the sum r+q equals between 1 and 10;

y is a whole number ranging between 1 and 3;

Q, N and the $R_j$ groups optionally form together one or more rings, said ring or rings optionally comprising one or more heteroatoms;

the group $(R_i-O)_n$ can be the same or different when n>1; and, the group can be the same or different when y>1.

20 Claims, 4 Drawing Sheets

THINNERS FOR AQUEOUS SUSPENSIONS OF MINERAL PARTICLES AND HYDRAULIC BINDER PASTES

The invention concerns the use of compounds comprising at least one phosphonic amino-alkylene group and at least one polyoxyalkylated chain, and their salts, as thinning agents.

The invention also concerns novel compounds comprising at least one phosphonic amino-alkylene group and at least one polyoxyalkylated chain, as well as their salts.

STATE OF THE ART

It is known to introduce thinners into aqueous suspensions of mineral particles to lower the viscosity or to reduce the water content of these suspensions. The suspensions concerned are notably suspensions of calcium salts, such as calcium carbonate or calcium sulfate, or suspensions of mineral oxides, such as titanium dioxide or iron oxide. It is only after having been thinned that these suspensions can be used for the preparation of various industrial products, such as paints, paper-coating products and formulations for rubbers and synthetic resins.

It is also known to add thinners to hydraulic binders, such as cements, plasters, calcium sulfates or lime, in order to reduce the water content of the hydraulic binder paste. As a result, the hydraulic binder paste has, after hardening, a denser structure. This is translated by a higher mechanical strength.

As can be understood somewhat easily in the particular case of paper coating, suspensions of mineral particles, in a general way, must have a low viscosity to facilitate their manipulation and their application while also having the highest possible content of mineral material, in order to reduce the quantity of calorific energy necessary for evacuation of their aqueous fraction by drying. Obtaining these qualities under acceptable economic conditions can generally only be accomplished by having recourse to thinners.

Also for economic reasons, thinners are required that permit obtaining very high and stable fluidities even when they are present in the suspension in very small quantities. But since numerous thinners proposed in the prior art, such as those based on polyelectrolytes, see their thinning effects diminish when the electrolyte content of the mixtures to be thinned increases, one is therefore obligated to increase the quantities of these thinners to reach the desired viscosity.

Also, thinners are sought, which, when they are used in complex mixtures, do not have a secondary function risking disturbing the characteristics of the mixture in question. Thus, in the field of hydraulic binders, for example, it is not sufficient that a thinner permits obtaining suspensions of hydraulic binder particles of a satisfactory fluidity. It is also necessary that its implementation permits setting of the hydraulic binder and obtaining a product of good quality.

In the field of compositions for drilling cement, European Patent Application No. 444,542 proposes using as thinners compounds corresponding to one of the formulas:

or in which x is greater than or equal to 10.

The presence of these compounds in drilling cement compositions must permit reducing the viscosity to the point of rendering said compositions pumpable under conditions of turbulent flow, even in the presence of salts.

The major disadvantage of these thinners resides in the extremely large setting delays that they generate.

As a result, they have very limited applications and they cannot be used when the desired setting time of the hydraulic binder paste must be relatively short.

Thinners are also known whose use less affects the setting time of hydraulic binder pastes with which they are mixed. The most well known are thinners based on resins obtained by condensation of sulfonated naphthalene with formaldehyde or by condensation of melamine with formaldehyde and a sulfonated compound.

Thus, European Patent No. 99,954 concerns water-soluble thinners obtained by condensation of amino-sulfonic acid having at least one aromatic nucleus with nitrogenated products carrying several amine functions and formaldehyde.

If these thinners do not delay in a notable manner the setting of hydraulic binders, they nevertheless have a limited activity and especially when the mixture to be thinned contains a non-negligible quantity of electrolyte. Another disadvantage of these thinners is that they can only be made available in the form of aqueous solutions at limited concentrations, generally at most equal to 40%, because an increase in the concentration increases the viscosity of these solutions, which limits their use.

Therefore, in the state of the art, no thinners exist that cumulatively fulfill the following conditions:
- packaging in a concentrated form or in a powdered form to facilitate storage and transport,
- great stability, even in concentrated solution,
- a high thinning capacity with regard to a large number of mineral particles of diverse chemical nature,
- a viscosity in concentrated solution that is sufficiently low, at ambient temperature, regardless of the season, so as to facilitate their use and eliminate all additional operations of the heating type,
- a viscosity of suspensions constant over time and which remains low despite the introduction of one or more electrolytes.

SUMMARY DISCLOSURE OF THE INVENTION

In a surprising manner, it has been discovered that the above-mentioned objectives are reached when one uses, as thinning agents for aqueous suspensions of mineral particles and hydraulic binder pastes, compounds (I) or salts of compounds (I), said compounds (I) corresponding to the following formula:

in which:

R is a hydrogen atom or a monovalent hydrocarbon group having 1 to 18 carbon atoms and possibly one or more heteroatoms, The $R_i$ groups are similar to or different from each other and represent an alkylene, such as ethylene, propylene, butylene, amylene, octylene or cyclohexene, or an arylene, such as styrene or methylstyrene; the $R_i$ possibly contain one or more heteroatoms, Q is a hydrocarbon group comprising 2 to 18 carbon atoms inclusive and possibly one or more heteroatoms, A is an alkylidene group comprising 1 to 5 carbon atoms inclusive, The $R_j$ groups are similar to or different from each other and can be chosen from among:
* the A-PO3H2 group, A having the above-mentioned meaning,
* the alkyl group comprising 1 to 18 carbon atoms inclusive and able to carry [R-O($R_i$-O)n] groups, R and $R_i$ having the above-mentioned meanings,
* and the group $R_k$ designating a group, such as, $R_j$, B designating an alkylene group having 2 to 18 carbon atoms inclusive, "n" is a number greater than or equal to 0, "r" is the number of [R-O($R_i$-O)$_n$] groups carried by all the $R_j$ groups, "q" is the number of [R-O($R_i$-O)$_n$] groups carried by Q, the sum "r+q" is comprised between 1 and 10 inclusive, "y" is a whole number comprised between 1 and 3 inclusive, Q, N, and the $R_j$ groups can form together one or more rings, this ring or these rings moreover able to contain one or more other heteroatoms.

The salts of compounds (I) can be stoichiometric or not, mixed or not, and are made up with alkali metals, alkaline-earth metals, amines or quaternary ammoniums.

Compounds (I) are present in a form able to vary from the liquid form to the solid form, passing through the waxy from.

They are generally soluble or dispersible in water.

Compounds (I) as well as their salts have never been described in the state of the art with the exception of those called compounds (II), for which, when one refers to the formula of compounds (I), it is found that:
* either
  R is the hydrogen atom and n is zero, with $R_i$, y, r, q, n, $R_j$, A and Q having the above-mentioned meanings
* or
  R is an alkyl having 1 to 5 carbon atoms inclusive and
  $R_i$ has 2 to 5 carbon atoms inclusive, and
  "y"=1, "r"=0, "q"=1, "n"≦20, and
  $R_j$=A-PO3H2, A having the above-mentioned meaning; $R_j$ can be combined in salt form, and
  Q has 3 to 5 carbon atoms inclusive,
* or
  R is a hydrogen atom and
  $R_i$ is an ethylene group and
  "y"=1, "r"=0, "q"=1, "n"=1 and
  $R_j$=A-PO3H2, A having the above-mentioned meaning; $R_j$ can be combined in salt form, and Q is an ethylene group.

These compounds (II) are known as corrosion inhibitors (U.S. Pat. No. 3,718,603), and as inhibitors of the formation of tartar deposits (U.S. Pat. Nos. 3,976,589 and 5,069,798).

As a result, the present invention also has for a subject novel compounds (III) and their salts, said compounds (III) corresponding to the family of compounds (I), with the exception of compounds (II). As a result, compounds (III) correspond to the following formula:

in which:

R is a hydrogen atom or a monovalent hydrocarbon group having 1 to 18 carbon atoms inclusive and possibly one or more heteroatoms.

The $R_i$ groups are similar to or different from each other and represent an alkylene, such as ethylene, propylene, amylene, octylene or cyclohexene or an arylene, such as styrene or methylstyrene. The $R_i$ groups possibly contain one or more heteroatoms;

Q is a hydrocarbon group having 2 to 18 carbon atoms inclusive and possibly one or more heteroatoms;

A is an alkylidene group having 1 to 5 carbon atoms inclusive;

The $R_j$ groups are similar to or different from each other and can be chosen from among:
* the -A-PO3H2 group, A having the above-mentioned meaning,
* an alkyl group having 1 to 18 carbon atoms inclusive and able to carry [R-O($R_i$-O)n] groups, R and $R_i$ having the above-mentioned meanings,
* and the group:

$R_k$ designating a group such as $R_j$,

B designating an alkylene group having 2 to 18 carbon atoms,

"n" is a number greater than or equal to 0, but n is different from 0 when R is the hydrogen atom, "r" is the sum of the [R-O($R_i$-O)n] groups carried by all the $R_j$ groups, "q" is the number of [R-O($R_i$-O)n] groups carried by Q, the sum "r+q" is comprised between 1 and 10 inclusive, "y" is a whole number comprised between 1 and 3 inclusive, Q, N and the $R_j$ groups can form together one or more rings; this ring or these rings can contain, moreover, one or more other heteroatoms, with the exception of compounds (I) and their salts for which:
* either
  R is an alkyl of 1 to 5 carbon atoms inclusive, and
  $R_i$ has 2 to 5 carbon atoms inclusive, and
  "y"=1, "r"=0, "q"=1, "n"≦20, and
  $R_j$=A-PO3H2, A having the above-mentioned meaning; $R_j$ can be combined in salt form, and
  Q has 3 to 5 carbon atoms inclusive,

* or

R is a hydrogen atom and $R_i$ is an ethylene group and

"y"=1, "r"=0, "q"=1, "n"=1 and $R_j$=A-PO3H2, A having the above-mentioned meaning; $R_j$ can be combined in salt form, and Q is an ethylene group In the same way as for the salts of compounds (I), salts of compounds (III) can be stoichiometric or not, mixed or not, and are made up of alkali metals, alkaline-earth metals, amines or quaternary ammoniums.

DETAILED DISCLOSURE OF THE INVENTION

Preparation of compounds (I)

With the exception of compounds (II) whose preparation is known, compounds (I) are, preferably, prepared from amino alcohols (A) according to the several-step process described below.

By amino alcohol is understood in the present disclosure a compound comprising at least one primary or secondary amine function and at least one OH group.

In a first step, a potassium amino-alcoholate (B) is prepared from an amino alcohol (A), in a known way preferably by contact with a base having one or more potassium cations.

Amino alcohols (A) that can serve as raw materials advantageously conform to the following formula:

in which:

"y" is the number of primary or secondary amine functions that are identical to or different from one another and "y" is comprised between 1 and 3 inclusive,

"r" is the number of OH groups carried by all of the $R_j$ groups,

"q" is the number of OH groups carried by Q,

"r+q" is comprised between 1 and 10 inclusive,

Q represents a hydrocarbon group having 2 to 18 carbon atoms inclusive, and possibly one or more heteroatoms, each $R_j$ group is a hydrogen atom or an alkyl radical having 1 to 18 carbon atoms inclusive, or a group of the type:

in which $R_k$ designates a group such as $R_j$ and B designates an alkylene group having 2 to 18 carbon atoms inclusive.

Q, N and the $R_j$ units can form together one or more rings, this ring or these rings being able, moreover, to contain one or more other heteroatoms.

Q and the $R_j$ groups must be free of groups able to react together or with other groups carried by amino alcohol (A) or amino-alcoholate (B) under the reaction conditions of the process described above.

Among amino alcohols (A) can be cited, by way of example, the following currently used compounds:
ethanolamine, diethanolamine, the propanolamines, N-methylethanolamine, amino-4-cyclohexanol, diamino-propanol-2, N-decylethanolamine, 1-(2-hydroxyethyl)piperazine, or the compounds conforming to the formulas: HO—$C_2H_4$-NH-$C_2H_4$-$NH_2$ or HO—$C_2H_4$-(NH-$C_2H_4$)$_n$-$NH_2$.

The base used is preferably diphenylmethylpotassium, potassium hydride, potassium amide or finely divided potassium. Such bases have the advantage of quantitatively transforming the alcohol functions into alcoholate functions at moderate temperature, for example, 30° C.

The use of such bases also permits, preparing amino-alcoholate (B) in a solvent in which the following steps can be conducted.

Bases such as potassium hydroxide or potassium alcoholates can also be used. But in this case, the formation reaction of amino-alcoholate presents several disadvantages:

this reaction is equilibrated, this reaction leads to the formation of water or light alcohol which it is necessary to eliminate from the reaction mixture, for example, by evaporation, before undertaking the following steps.

In a second step, the amino-alcoholate previously obtained is reacted with an oxirane corresponding to $R_iO$ or several oxiranes simultaneously or successively, in an aprotic and anhydrous solvent, under an anhydrous atmosphere and at a temperature comprised between 0° C. and 200° C., so as to attach onto each oxygen atom originating from an alcoholate function, a series of "n" similar or different $R_iO$ groups. The oxiranes corresponding to $R_iO$ can be chosen from the group made up of ethylene oxide, propylene oxide, butylene oxide, amylene oxide, octylene oxide, styrene oxide, methylstyrene oxide, cyclohexane oxide, their various substituted derivatives and their mixtures.

The quantity of oxirane used is a function of the length "n" of the desired chains and the number of OH groups of the initial amino alcohol (A).

The oxirane can be introduced progressively into the reaction medium. One can thus control the degree of polyoxyalkylation, which offers the advantage of being able to vary the hydrophilic or hydrophobic character of the molecule. It is sufficient, in fact, to interrupt the addition of oxirane as soon as the desired average length of the polyoxyalkylated chains is reached.

The addition of oxirane is conducted in a solvent free of acid hydrogen under the operating conditions, in order not to regenerate the alcohol functions.

The solvent is preferably chosen from among high-polarity solvents in order to facilitate the dissociation of potassium cations from the alcoholate functions. Particularly well suited solvents are tetrahydrofuran, diglyme (diethylene glycol dimethyl ether), dimethyl sulfoxide or hexamethylphosphoramide.

The oxirane addition reaction must be effected under anhydrous atmosphere in order to prevent the introduction of water into the reaction medium, which would regenerate the alcohol functions and therefore disturb the polyaddition. For this, one can work under nitrogen, argon or under any other gas inert with regard to the reaction medium.

The reaction temperature of this second step is generally comprised between 0° C. and 200° C. according to the solvent used and preferably between 20° C. and 120° C.

The reaction durations and pressures are known to the expert and are a function of the operating mode followed.

In a third step, the previously obtained product is neutralized or functionalized in a manner known in and of itself, by attaching a hydrogen atom or an alkyl radical onto each oxygen atom terminating a polyoxyalkylated chain.

Therefore the reaction medium can be acidified to attach a proton or add an alkylation agent, such as dimethyl sulfate or methyl iodide to realize an alkylation. The agent used to effect this functionalization must, however, be chosen by taking into account the presence of amine functions, in order not to affect them.

After evaporation of the solvent and the water, a polyoxyalkylated amine is obtained that is then functionalized in a fourth step according to the Mannich reaction described notably in the Journal of Organic Chemistry (Vol. 31, 1603–07, 1966), or according to French Patent No. 1,342, 412 or U.S. Patent No. 3,567,768.

During said fourth step, it is recommended, to prevent the degradation of the polyoxyalkylated chain or chains, to work with proportions close to stoichiometry for acid and formol, and to slowly introduces the formol into the reaction medium.

From the Mannich reaction, the compounds are in practice obtained in the form of ammonium. They can be used in this form or be neutralized so as to eliminate their acid character.

The salts of these compounds are prepared in a way known in and of itself, by total or partial neutralization with an appropriate base or mixture of bases.

Among compounds (I) can be cited those represented by the formulas:

$$HO-(C_2H_4O)n-C_2H_4-N-C_2H_4-N\begin{smallmatrix}CH_2-PO_3H_2\\ \\CH_2-PO_3H_2\end{smallmatrix}$$
$$\begin{smallmatrix}|\\CH_2\\|\\PO_3H_2\end{smallmatrix}$$

(R = H, Ri = C$_2$H$_4$, Q = C$_2$H$_4$, A = CH$_2$, Rj = CH$_2$CH$_2$N[CH$_2$—PO$_3$H$_2$]$_2$)

and $$HO-(C_2H_4O)n-C_2H_4-N\begin{smallmatrix}CH_2-PO_3H_2\\ \\CH_2-PO_3H_2\end{smallmatrix}$$

Use of Compounds (I)

As specified above, compounds (I) and their salts procure an equally good thinning effect for aqueous suspensions of mineral particles not leading to hydraulic setting as well as for hydraulic binder pastes.

By aqueous suspension of mineral particles, an aqueous suspension is understood in the present disclosure, which [suspension] contains particles without hydraulic setting, such as calcium fillers, such as, for example, calcium carbonate or dihydrated calcium sulfate, slaked lime or calcium fluoride; mineral oxides, such as, for example, chromium oxide, silica, alumina or iron oxide; other mineral fillers such as silicates, including mica, etc. By hydraulic binder pastes is understood pastes comprising notably cements, such as Portland cements or aluminous cements, plasters such as α or β plasters, quicklime, pure phases of C3S, C4AF, C3A, C12A7, CA, C2A cements or mixtures of these pastes. The aqueous suspensions of mineral particles and the hydraulic binder pastes concerned by the invention may possibly contain various additives.

By way of example of additives, one can cite suspension stabilization agents, such as cellulose ethers or xanthan gums, alkaline silicates for sprayed concrete, setting and hardening accelerators and retarders.

According to the invention, one preferably uses compounds (I) or their salts for which R is a hydrogen atom or a methyl, ethyl or nonylphenol group or a saturated or unsaturated hydrocarbon group having 12 to 18 carbon atoms. More preferably, R is a hydrogen atom.

The $R_i$ groups are in a preferential manner chosen from among ethylene and propylene. It is even more desirable that the $R_i$ groups be primarily, even solely, ethylene, and in sufficient number to conserve the water-soluble or water-dispersible character of compounds (I) or their salts.

The group Q is determined by the choice of initial amino alcohol (A). Preferably, it has 2 to 12 carbon atoms (inclusive), and more preferably, it has 2 to 6 carbon atoms (inclusive). Advantageously, Q is chosen from among ethylene, cyclohexene or n-hexene.

The alkylidene group A which is the carrier of one divalent carbon atom has preferably 1 to 3 carbon atoms (inclusive). It is particularly advantageous that A be the methylene group.

The $R_j$ group, which is possibly combined in salt form, is chosen preferably from among the -CH$_2$-PO$_3$H$_2$, methyl, and C$_2$H$_4$N(CH$_2$PO$_3$H$_2$)$_2$ groups. More preferably still, $R_j$ represents the -CH$_2$-PO$_3$H$_2$ group.

It is desirable that "n" be comprised between 1 and 10,000 inclusive. It is particularly preferred that the values of "n" are comprised between 1 and 500 inclusive. In the ideal case, a value for "n" will be chosen comprised between 1 and 250 inclusive.

The sum "r+q" corresponds to the total number of polyoxyalkylated chains. Preferably, this sum is less than 3. More preferably, it is equal to 1.

"y" is a number comprised between 1 and 3 inclusive. It is preferably equal to 1 when the thinner is intended for classical hydraulic binder pastes with which setting delays are not desired.

In addition, but for economical reasons in this case, "y" will preferably be chosen equal to 1 for a thinner designed for aqueous suspensions of mineral particles without hydraulic setting.

On the other hand, in hydraulic binder compositions for which a setting delay is desired, such as, for example, drilling cement compositions, "y" will be preferably chosen equal to or greater than 1.

The salts of compounds (I) are preferably sodium, calcium or diethanolamine salts.

The use according to the invention of compounds (I) or their salts makes it possible to obtain very fluid aqueous compositions of mineral particles even when they are highly charged.

One of the major advantages of compounds (I) or their salts resides in the fact that they procure a notable thinning effect with regard to a great diversity of fillers, with the reservation, however, that these fillers do not have, superficially at least, a hydrophobic character generally resulting from a treatment. Thus, the thinners of the invention are particularly efficacious in aqueous compositions of mineral fillers without hydraulic setting, such as, for example, calcium fillers, such as calcium carbonate or dihydrated calcium sulfate, slaked lime, or calcium fluoride; mineral oxides, such as titanium dioxide, ferric oxide, chromium oxide, silica or the aluminas; or other fillers, such as silicates, such as, for example, mica, etc.

In these aqueous compositions of mineral fillers without hydraulic setting, possibly containing various additives known to the expert, the thinners of the invention can be incorporated therein in a proportion comprised between 0.01% and 25% inclusive, preferably less than 5% according to the desired fluidity, the percentage being expressed in mass of dry thinner with regard to the mass of dry mineral.

Compounds (I) or their salts as thinners also have a great efficacy with regard to cement pastes composed of one or more hydraulic binders, water and various additives and fillers known to the expert.

Moreover, it is surprisingly observed that the increased fluidity obtained by means of compounds (I) or their salts is maintained over time for a longer duration that that which is observed with the thinners known up until now. Compounds (I) or their salts can thus be used as fluidity maintenance agents, for example, in combination with other additives, in particular, other thinners, or by introducing them into already fluid hydraulic suspensions.

However, it is observed that under certain conditions, compounds (I) or their salts may give rise to effect a delay of the setting, this additional effect possibly being desirable in specific applications, such as those of cements sufficiently fluid to be pumpable and transportable, such as drilling cements, or, in contrast, undesirable in more classical cement compositions.

Advantageously, compounds (I) or their salts have a setting delay effect for hydraulic binders that can be modulated, which, depending on to the case, can be very limited, and even undetectable, and which, in other contrary cases, will guarantee workability for a long time.

This is why we recommend to obtain a setting delay effect, using compounds (I) or their salts conforming to at least one of the two following conditions ($a_1$) or ($b_1$):

($a_1$) "y" is greater than 1,
($b_1$) "y" is equal to 1 and $R_j$ comprises at least one phosphonic function or phosphonate.

More preferably, we also recommend, in order to obtain a setting delay, retaining one and/or the other of the following conditions:

($c_1$) "n" is less than or equal to 100,
($d_1$) a proportion of compounds (I) or their salts greater than that of one of conditions ($a_1$), ($b_1$) and ($c_1$) is not verified.

The delay effect of compounds (I) or their salts fulfilling at least one of conditions ($a_1$), ($b_1$), ($c_1$), or ($d_1$), and preferably all of these conditions, can therefore be advantageously and profitably used, instead of the use of other setting retarders. More preferably still, compounds (I) or their salts are chosen fulfilling conditions ($a_1$) and ($c_1$), with at least two phosphonic functions or phosphonates, as soon as a setting delay is desired.

On the other hand, the thinners of the invention, which are incorporated into cement pastes called classical, composed of one or more hydraulic binders, water and various additives and fillers known to the expert, and in which it is not desirable to delay setting, will preferably be chosen from among compounds (I) or their salts fulfilling the following two conditions:

($a_2$) "y" is equal to 1;
($b_2$) "n" is greater than or equal to 100.

Moreover, compounds (I) or their salts will lead to better fluidity and final desired mechanical strength if they are carriers of two phosphonic functions and/or phosphonates.

In cement pastes called classical, compounds (I) or their salts can be incorporated in a proportion comprised between 0.01% and 25% inclusive, preferably less than 5%, the percentage being expressed by mass of dry additive with regard to the mass of binder contained in the cement pastes.

Of course, it is also possible to use a mixture of compounds (I) or their salts with short chain (n<50) and compounds with long polyoxyalkylated chain (n>50) so as to obtain the optimal effects in terms of fluidity and setting delay. Such a mixture can permit, moreover, dissolving or dispersing compounds (I) or salts of compound I, which would be insufficiently soluble or insufficiently dispersible in water, for example, because their polyoxyalkylated chain is too short or the Q group is too large.

It goes without saying that the use of compounds (I) or their salts is not opposed to the simultaneous use of other known additives.

Other advantages and objectives of the invention will appear more clearly upon reading of the examples given below for illustrative and non-limiting purposes.

EXAMPLES

Examples 1 and 2 concern the preparation of compounds (I).

Examples 3 to 5 relate to evolutions of the viscosity of aqueous suspensions of $CaCO_3$ as a function of various parameters, such as the nature of the additive, the quantity of additive added, or the length of the polyoxyalkylated chains. The filler, which is the subject of these tests, is $CaCO_3$ sold by SOLVAY and having a large specific surface, of the order of 22 $m^2/g$. Tests similar to Examples 3 to 5, realized on $CaCO_3$ with a smaller specific surface (approximately 0.6 $m^2/g$) have also permitted establishing the efficacy of the additives tested.

Examples 6 to 11 illustrate the use according to the invention of compounds (I) as thinners for hydraulic binders.

Examples 12, 13, 15 and 16 illustrate the thinning capacity of compounds (I) according to the invention with regard to various mineral fillers.

Example 14 shows the insensitivity of the compounds of the invention in the presence of salts.

Example 17 illustrates the setting delay effect, which the use of certain compounds (I) brings about.

EXAMPLE 1 a) Synthesis of the compound corresponding to the formula:

(b1)  (a1)  (a2)  (c)  (b2)

500 cm³ of anhydrous tetrahydrofuran and 1.22 g (0.02 mole) of ethanolamine are introduced under argon into a perfectly anhydrous glass reactor. A solution of diphenylmethylpotassium, or 21.2 cm³ of a solution titrated exactly at 0.95 mole/L (0.02 mole), is added dropwise under argon until obtaining a persistent orange-brown color of the medium. There is partial precipitation of the potassium amino-alcoholate.

Holding the argon inlets and outlets closed, ethylene oxide, or 51 cm³ (1 mole at 20° C.), is introduced in liquid form, and then the reactor is brought to 30° C. The reactor is then maintained at an overpressure of approximately 0.2 bar and the mixture is kept stirred at 30° C. for 12 hours. At the end of the reaction, the mixture assumes a copper color. It is acidified by a 2% methanol solution in hydrochloric acid.

Neutralization is obtained when the medium is decolored into clear yellow. The potassium chloride is eliminated by filtration, the tetrahydrofuran (THF) is evaporated under vacuum, and the residue is poured into a mixture made up of 800 cm³ water and 800 cm³ ether.

The aqueous phase contains the specifically polyoxyethylated aminated polymer on the oxygen of the alcohol function, of which 45 g are isolated after total evaporation of the water under vacuum.

By $^1$H NMR (proton nuclear magnetic resonance) in deuterated chloroform, the following peaks are found:

a multiplet at 3.64 ppm corresponding to 202H designated by a1 and a2, a singlet at 3.05 ppm corresponding to 3H designated by b1 and b2, a triplet at 2.70 ppm corresponding to 2H designated by c.

The absence of polymer produced by condensation of ethylene oxide on the amine function is demonstrated by the absence of a singlet at 2.35 ppm, which would correspond to the presence of a methyl on a secondary nitrogen. Gel permeation chromatography (GPC) in water provides a chromatogram (previously calibrated by a standard polyoxylethylene range) whose maximum is situated at Mw=2, 300 g/mole, in agreement with the mass expected.

b) Synthesis of the diphosphonated compound corresponding to the formula:

226 g (0.1 mole) of the compound obtained from step a), 16.4 g (0.2 mole) of crystallized phosphorous acid and 12 g (0.11 mole) of hydrochloric acid in 35% aqueous solution are introduced into a one-liter, three-necked flask equipped with a coolant.

The mixture is heated with stirring up to 100° C., and then over five hours, 17.8 g (0.22 mole) of a 37% aqueous solution of formaldehyde are introduced, and it is heated to reflux for seventeen hours.

The reaction medium is then poured into 900 cm³ of cold water, and the dry matter content is adjusted to 30% by dilution.

Analysis of the proton nuclear magnetic resonance spectrum (NMR) indicates the presence of a doublet at 3.55 ppm corresponding to 4 atoms of hydrogen (N—$CH_2$P), a triplet at 3.7 ppm corresponding to 2 atoms of hydrogen ($CH_2$-N), and a multiplet at 3.64 ppm corresponding to 202 hydrogen atoms.

EXAMPLE 2

The compound corresponding to the formula:

has been prepared according to the operating mode described in Example 1, from 0.1 mole of N-methylethanolamine, 0.1 mole of diphenylmethylpotassium, and 5 moles of ethylene oxide.

a) The $^1$H-NMR of the intermediate product, i.e., the polyoxyethylated amine obtained before the Mannich reaction (proton nuclear magnetic resonance), in the deuterated chloroform comprises: 1 singlet at 2.4 ppm (N—CH$_3$) (3H); 1 triplet at 2.7 ppm (N—CH$_2$) (2H); 1 singlet at 3.64 ppm (CH$_2$CH$_2$O)n (202H) and 1 singlet at 3.1 ppm (N—H and O—H) (2H).

The absence of polymer produced by condensation of ethylene oxide on the amine function is demonstrated by the absence of a singlet at 2.3 ppm which would correspond to the presence of a methyl on a tertiary nitrogen. Gel permeation chromatography (GPC) in water provides a chromatogram (previously calibrated by a standard polyoxyethylene range) whose maximum is situated at Mw=2,350 g/mole, in agreement with the mass expected.

b) This intermediate product has been functionalized according to part b) of Example 1.

EXAMPLE 3

Evolution of the viscosity as a function of the quantity of additive added and the number of phosphonic functions

Measurements of the viscosity of suspensions containing 80 g of water, 20 g of CaCO$_3$ with large specific surface: 22 m$^2$/g sold by SOLVAY under the reference SOCAL 31, and variable quantities of thinner to be tested were effected.

The compounds tested, prepared according to Example 1 or Example 2 are the following:

* compound (a) used by way of comparison, (not conforming to formula (I))

Figure 1:
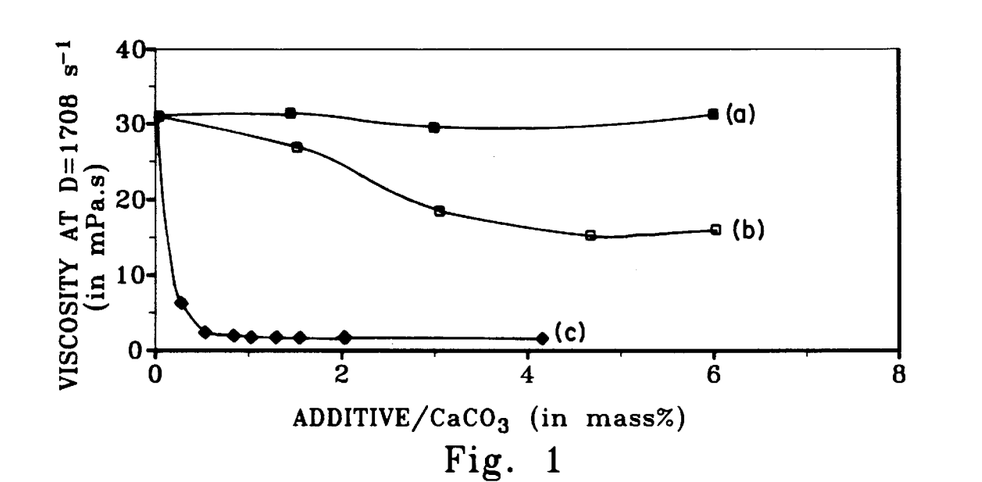
FIG. 1 is a graph showing the evolution of the viscosity of a suspension containing 80 g of water, 20 g of $CaCO_3$ and variable quantities of thinner as a function of the quantity of three different thinners (designated comparative compound a, compound b and compound c) introduced into the suspension.

*compound (b) of the formula:

*compound (c) of the formula:

FIG. 1 shows 3 curves representing the evolution of the viscosity of the suspension (expressed in mPa.s), obtained with a level of shearing of 1,708 s$^{-1}$, as a function of the quantity of additive (compound a, b or c) introduced into the suspension.

As can be seen, compounds (b) and (c) bring about a significant reduction of the viscosity of the suspension, and this is effected even starting with small contents of additive. This reduction is particularly significant when this additive has a diphosphonated end (additive c).

Beyond a certain proportion, which is a function of the length and the nature of the polyoxyalkylated chain, supplementary additions of thinners (b) or (c) do not bring about an appreciable increase of fluidity: it is observed, in fact, that beyond a certain proportion of thinner (b) and (c), the fluidity remains almost constant and the level of fluidity reached depends on the nature of the thinner introduced.

EXAMPLE 4

Evolution of the viscosity as a function of the quantity of additive added and of the length of the polyoxyalkylated chains Measurements of viscosity were effected with three compounds corresponding to formula (I), differing only by the length of their polyoxyethylated chain:

*a compound d (n=1) of formula

*a compound e (n=10) of formula

Figure 2:
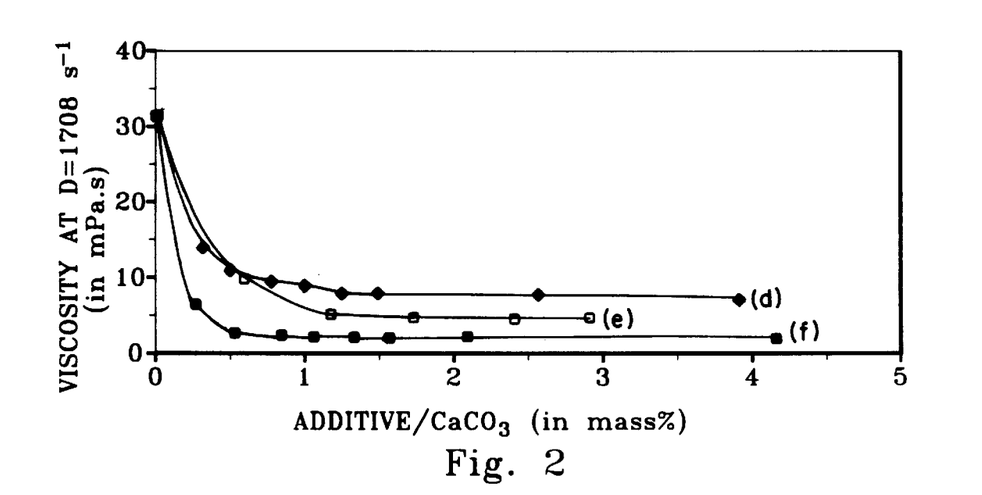
FIG. 2 is a graph showing the evolution of viscosity of a suspension containing 80 g of water, 20 g of $CaCO_3$ and variable quantities of thinner as a function of the quantity of three different thinners (designated compound d, compound e and compound f) introduced into the suspension.

*a compound f (n=50) of formula:

The suspensions tested contained 80 g of water, 20 g of CaCO$_3$ and variable quantities of additive (compound d, e or f). FIG. 2 shows three curves representing the evolution of viscosity (in mPa.s), at an amount of shearing of 1,708 s$^{-1}$, as a function of the quantity of thinner introduced.

Beyond a certain quantity of additive added, a threshold appears, and the viscosity practically does not vary any longer from this point.

Moreover, it is observed that the longer the polyoxyethylated chain, the greater the thinning capacity.

However, the increase of thinning capacity is not unlimited. In fact, beyond a certain value of "n", the thinning capacity is stabilized, as is explained in the following example.

EXAMPLE 5

Evolution of the viscosity solely as a function of the length of the polyoxyalkylated chains Several suspensions were made with 80 g of water, 20 g of CaCO$_3$ and at each time the same quantity of thinner to be tested, in this case, 0.24 g (or 1.2% by weight with regard to the quantity of CaCO$_3$).

Compounds corresponding to formula (I) prepared according to Example 1 from ethanolamine and differing only by the length of their polyoxyalkylated chain were tested.

The quantity of compound present in the suspension has been chosen so as to reach an almost constant viscosity despite a supplemental addition of the compound being set by a threshold on the viscosity curves as a function of the quantity of thinner.

Figure 3:
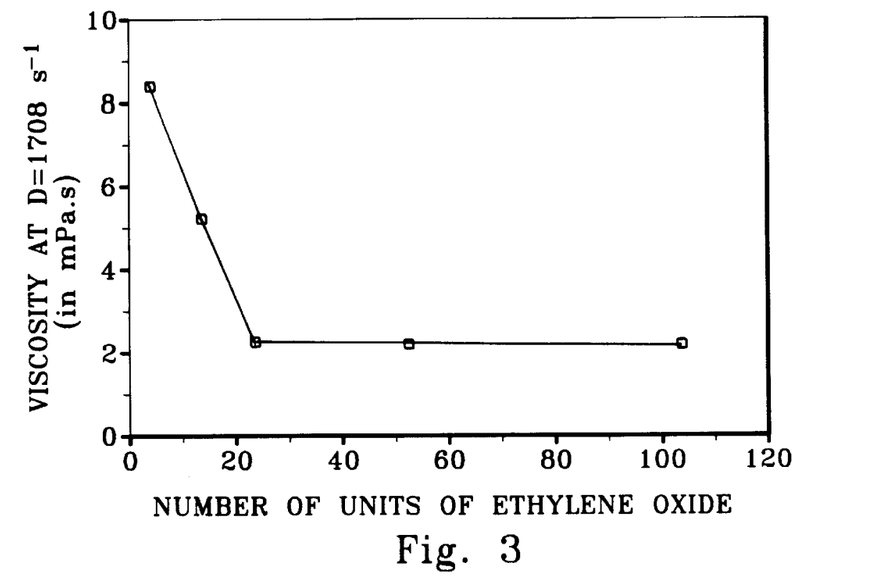
FIG. 3 is a graph showing the evolution of viscosity of a suspension 80 g of water, 20 g of $CaCO_3$ and a quantity of thinner equivalent to 1.2% by weight the quantity of $CaCO_3$ for five thinners differing only as to the length of their polyoxyalklyated chains as a function of the number of ethylene oxide units in the polyoxyalklyated chain.

Curve 3 illustrates the evolution of the viscosity corresponding to this threshold as a function of the number "n":

Therefore, it appears that for this mineral, beyond a value "n" close to 20, the viscosity becomes almost constant.

However, this is only true in the case where the mineral particles in suspension are of similar size or, in other words, correspond to a narrowly selected particle-size fraction.

EXAMPLE 6

Compounds C1 to C10 corresponding to formula (F) given below have been synthesized according to Example 1 or Example 2 from the corresponding primary or secondary amino alcohols, then neutralized in a known way (of course when M=H, the compound is present in the form of ammonium). Their structural characteristics are given in Table (I) below.

Formula (F)

TABLE (I)

| Products | n | $M^+$ | $R_i$ |
|---|---|---|---|
| C1 | 10 | $H^+$ | $CH_3$ |
| C2 | 10 | $H^+$ | $-CH_2-PO(OM)_2$ |
| C3 | 50 | $H^+$ | $CH_3$ |
| C4 | 100 | $H^+$ | $CH_3$ |
| C5 | 100 | $H^+$ | $-CH_2-PO(OM)_2$ |
| C6 | 100 | $Na^+$ | $-CH_2-PO(OM)_2$ |
| C7 | 100 | $Ca^+$ | $-CH_2-PO(OM)_2$ |
| C8 | 100 | $DEAH^+$ | $-CH_2-PO(OM)_2$ |
| C9 | 170 | $H^+$ | $-CH_2-PO(OM)_2$ |
| C10 | 1 | $H^+$ | $-CH_2-PO(OM)_2$ |

*$DEAH^+$ represents the cation $(HOC_2H_4)_2 NH_2^+$

EXAMPLE 7

The thinning capacities of the compounds obtained in Example 6 have been evaluated by means of water reductions that they have brought about during the preparation of samples of the same plasticity.

The samples tested are composed of:

1) standardized mortar, i.e. 450 g of HP Havre cement and 1350 g of AFNOR sand (0–2 mm);
2) 0.3% by mass (1.35 g) of tested thinner with regard to the weight of the cement (except when a control sample is involved);
3) the quantity "x" of water (expressed in g) necessary for the sample to have the reference plasticity.

The chosen reference plasticity is that obtained when the control sample contains 225 g of water.

The reduction of water is the value, (225−x)/225. The workability of the sample has been measured with the mortar workability meter, according to the standard NF p 18-452.

The results obtained are compiled in Table (II) below:

TABLE (II)

| COMPOUNDS | WORKABILITY in s | WATER REDUCTION in % |
|---|---|---|
| C2 (diphosphonated) | 1.4 | 28 |
| C5 (diphosphonated) | 1.4 | 21 |
| C1 (monophosphonated) | 1.9 | 12 |
| C3 (monophosphonated) | 1.9 | 14 |
| C4 (monophosphonated) | 1.9 | 12 |
| control | 1.7 | 0 |

Therefore, a particularly high reduction of water is observed when the compound tested is diphosphonated.

EXAMPLE 8

The thinner capacities and mechanical strengths induced by compounds (I) were compared with performances resulting from the use of a commercial thinner.

The chosen commercial thinner is GT resin sold by the CHRYSO company. It comprises a polysulfonate based on melamine. The GT resin is measured in equivalent dry extract.

The water reduction and workability measurements were conducted as in Example 7, with the difference that the samples only contained 0.24% thinner.

Measurements of mechanical strength were effected according to the standard EN 196.

The results have been compiled in Table (III) below:

TABLE (III)

| COMPOUND | WORKABILITY (in s) | WATER REDUCTION (in %) | COMPRESSIVE STRENGTH (in mPa) after | | |
|---|---|---|---|---|---|
| | | | 1d | 7d | 28d |
| Control | 4.0 | 0 | 20 | 54 | 67 |
| GT resin | 4.1 | 7 | 24 | 60 | 70 |
| C5 (diphosphonated) | 3.6 | 20 | 24 | 67 | 80 |
| C9 (diphosphonated) | 3.7 | 17 | 24 | 62 | 74 |

EXAMPLE 9

In order to determine the influence of the nature of the $M^+$ cation of formula (F), water reduction, workability and compressive strength measurements were conducted, as in Example 7, with several compounds differing only by the nature of the $M^+$ cation.

Table (IV) below compiles the results obtained:

TABLE (V)

| COMPOUND | DOSAGE | WORKABILITY (in s) | M+ | WATER REDUCTION (in %) | COMPRESSIVE STRENGTH (in mPa) after 1d | 7d | 28d |
|---|---|---|---|---|---|---|---|
| C5 | 0.24% | 3.6 | H+ | 16 | 20 | 66 | 76 |
| C6 | 0.24% | 4.5 | Na+ | 17 | 20 | 63 | 79 |
| C7 | 0.24% | 3.3 | Ca+ | 19 | 20 | 62 | 77 |
| C8 | 0.24% | 3.3 | DEAH+ | 18 | 20 | 64 | 86 |
| control | 0.24% | 4.0 | / | 0 | 17 | 47 | 70 |

We therefore observe very high mechanical properties when M+ is the DEAH+ cation $(HOC_2H_4)_2NH_2^+$.

EXAMPLE 10

The thinning capacity as well as the mechanical strength induced by compounds (I) during their use according to the invention were compared with those obtained with the GT resin defined in Example 8.

The samples tested are formed from a mixture composed of:

concrete comprising:
  690 kg of gravel 10/20 mm rounded stones
  530 kg of gravel 4/10 mm rounded stones
  100 kg of gravel 1/4 mm rounded stones
  434 kg of gravel 0/1 mm rounded stones
  350 kg of HP Havre cement
  0.24% by mass thinner with regard to the weight of cement, except the control sample which does not contain thinner,
  and the quantity "x" of water (expressed here in kg) necessary so that the sample has the reference plasticity, defined here as being that of a control sample containing 183.7 kg of water.

The water reduction was calculated as in Example 7.

The fluidity was measured directly, i.e., by measuring the "slump" according to standard NF P-18-333.

The compressive strength was measured according to standard EN 196.

The results obtained are compiled in Table (V) below:

TABLE (V)

| THINNER | SLUMP | WATER REDUCTION (in %) | COMPRESSIVE STRENGTH (in mPa) after 1d | 7d | 28d |
|---|---|---|---|---|---|
| GT resin | 5 | 4 | 22 | 40 | 46 |
| C5 | 7 | 13 | 27 | 47 | 56 |
| C9 | 7 | 13 | 22 | 40 | 53 |
| Control | 7 | 0 | 21 | 38 | 44 |

As can be observed, compounds C5 and C9 bring about both a better water reduction and better mechanical properties than those obtained with GT resin.

The workability over an extended time of thinners C5, C9 and of the resin has been evaluated on a composition of concrete comprising:

605 kg of gravel 10/20 mm crushed
  515 kg of gravel 4/10 mm crushed
  165 kg of gravel 1/4 mm crushed
  340 kg of gravel 0/1 mm crushed
  175 kg of gravel 0/0.5 mm crushed
  350 kg of Cormeilles CPA HP cement
  a quantity of water necessary so that the sample has the reference plasticity defined here as being that of a control sample containing 166.7 liters.

The slump was measured according to standard NF P-18-333. The results obtained are compiled in Table (VI) below:

TABLE (VI)

| | | | SLUMP | | | |
|---|---|---|---|---|---|---|
| THINNER | DOSAGE (1) in % | T° | T° + 30 min | $T_F$ (2) | $T_F$ + 30 min | $T_F$ + 60 min | Comp. str. (3) in mPa |
| GT resin | 0.24 | 3 | 2 | 18 | 7 | — | 23.7 |
| C5 | 0.180 | 4 | 3 | 18 | 16 | 14 | 21.7 |
| C9 | 0.195 | 4 | 3 | 17 | 14 | 10 | 21.6 |

(1) in proportion to the quantity of cement,
(2) the thinner is added at $T_F = T° + 3.0$ min
(3) compressive strength at 24 h according to the standard NF P-18406.

By means of thinners C5 and C9, the working time of the concrete is increased, because the slump decreases only very slowly when compared to observations made for commercial thinners.

EXAMPLE 11

In this example, the water reduction, the compressive strength as well as the flexural strength are measured according to standardized EN 196, generated by compounds C1 and C10 in a standardized mortar (defined in Example 7).

Table (VII) below compiles the results obtained:

TABLE (VII)

| COMPOUNDS | DOSAGE | WORK-ABILITY (in s) | WATER REDUCTION (in %) | COMPRESSIVE STRENGTH (in mPa) | | FLEXURAL STRENGTH (in mPa) | |
|---|---|---|---|---|---|---|---|
| | | | | 7 days | 28 days | 7 days | 28 days |
| Control | | 4.2 | 0 | 46.3 | 68.3 | 11.2 | 12 |
| C1 | 0.195 | 4.1 | 20 | 60.5 | 78.3 | 13.1 | 13.4 |
| C10 | 0.210 | 4.3 | 20 | 65.5 | 89.8 | 13.4 | 14.1 |

Therefore excellent water reduction and excellent mechanical properties for both compressive and flexural strength are obtained with C1 and C10.

EXAMPLE 12

Viscosity measurements were effected in an aqueous suspension of $Cr_2O_3$, after 5 min stirring, as a function of the quantity of C5 thinner of the formula $HO-(CH_2CH_2O)_{100}-CH_2CH_2-N(CH_2-PO_3H_2)_2$. The $Cr_2O_3$ tested is a mineral pigment sold by BAYER under the name OXYDE DE CHROME VERT [green chromium oxide], Type GX, containing 99–99.5% $Cr_2O_3$ (DIN 55905) and dominant particle size of 0.35 micron.

Figure 4:
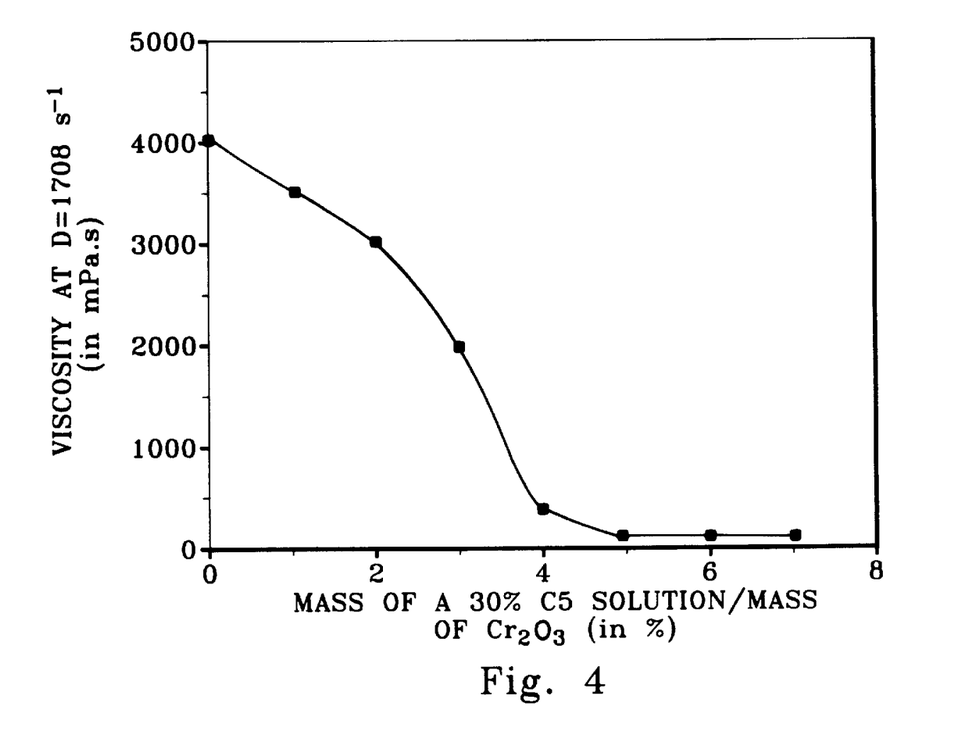
FIG. 4 is a graph showing the evolution of viscosity of a suspension containing 200 g of $Cr_2O_3$, 133.3 g of water and variable quantities of C5 thinner of the formula HO-$(CH_2CH_2O)_{100}$-$CH_2CH_2$-$N(CH_2$-$PO_3H_2)_2$, the water introduced with the thinner being subtracted to keep a constant water/mineral mass ratio, as a function of the quantity of C5 thinner introduced into the suspension.

The suspensions tested contained 200 g of $Cr_2O_3$, 133.3 g of water and variable quantities of C5 thinner, the water introduced with the thinner being subtracted to keep a constant water/mineral mass ratio. FIG. 4 shows the evolution of the viscosity (in mPa.s) of an aqueous suspension of 60% $Cr_2O_3$ as a function of the quantity of thinner introduced.

EXAMPLE 13

Figure 5:
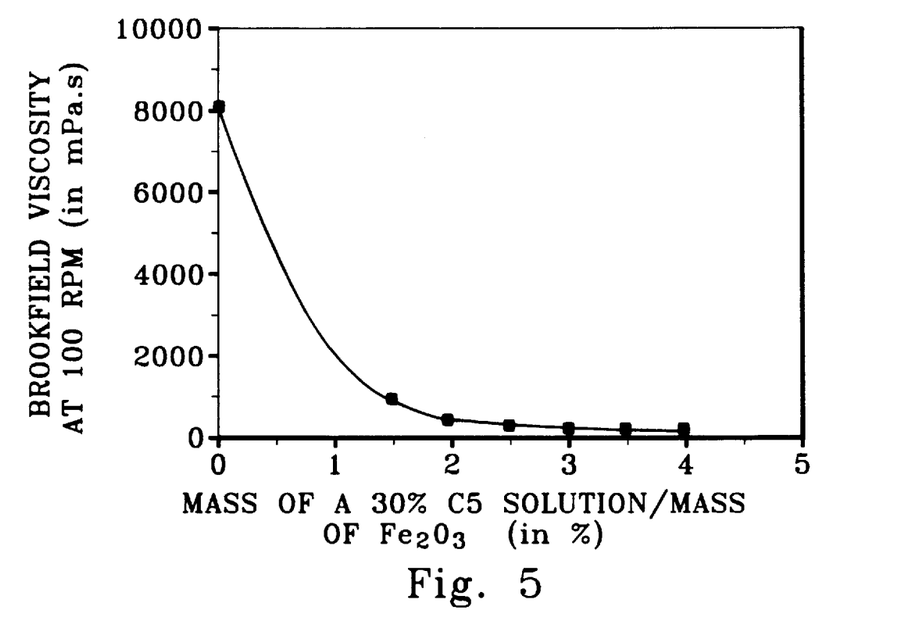
FIG. 5 is a graph showing the evolution of viscosity of a suspension containing 200 g of $Fe_2O_3$, 133.3 g of water and variable quantities of C5 thinner, the water introduced with the thinner being subtracted to keep a constant water/mineral mass ration, as a function of the quantity of C5 thinner introduced into the suspension.

Under the operating conditions of Example 12, measurements of the viscosity were effected in an aqueous suspension of $Fe_2O_3$, after 5 min of stirring, as a function of the quantity of C5 thinner. The $Fe_2O_3$ tested is a mineral pigment sold by BAYER under the trade name BAYFER-ROX brown of type 610, containing 90–91% $Fe_2O_3$ and dominant particle size of 0.3–0.6 micron. The suspensions tested contained 200 g of $Fe_2O_3$, 133.3 g of water and variable quantities of C5 thinner, the water introduced with the thinner being subtracted to keep a constant water/mineral mass ratio. FIG. 5 shows the evolution of the viscosity (in mPa.s) as a function of the quantity of thinner introduced.

EXAMPLE 14

This example illustrates the insensitivity of compounds (I) according to the invention, in this case compound C5 (described notably in the preceding example), in the presence of salts in water. The behavior of the C5 thinner is compared to that of the thinner sold by the COATEX company under the tradename AB100: it comprises a sodium polyacrylate, usually used to thin $CaCO_3$ suspensions.

An aqueous solution containing 50% by weight $CaCl_2$ is progressively added into an aqueous suspension containing 120 g of $CaCO_3$ (sold by Solvay and of specific surface of the order of 22 $m^2/g$), 180 g of water and 1.2 g of thinner.

Figure 6:
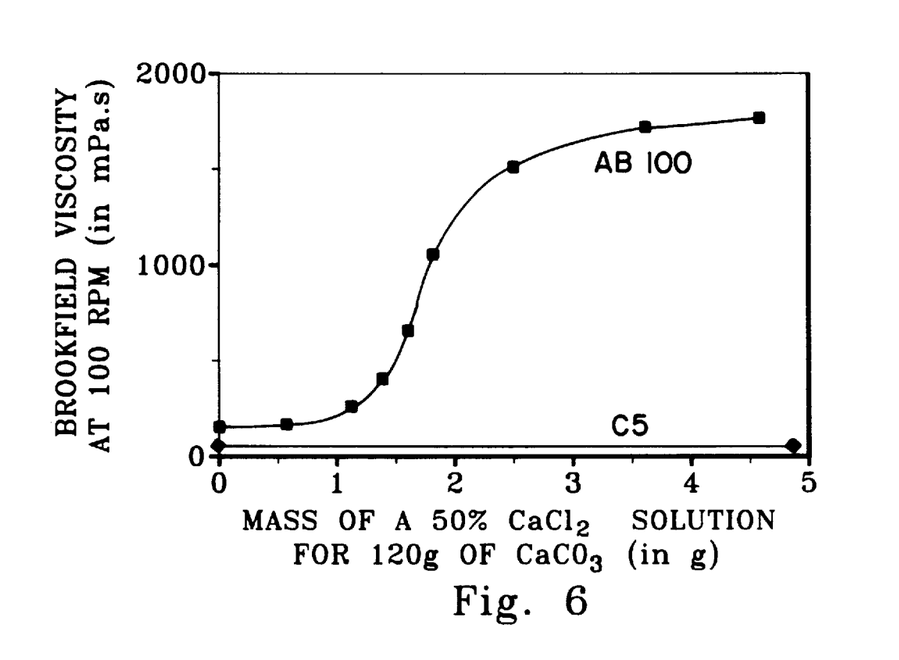
FIG. 6 is a graph showing the evolution of viscosity of an aqueous solution containing 120 g of $Cr_2O_3$, 180 g of water, 1.2 g of C5 or AB100 thinner, and variable quantities of a 50% aqueous solution $CaCl_2$ added thereto, as a function of the quantity of 50% $CaCl_2$ solution incorporated into the final aqueous solution.

The two curves shown in FIG. 6 show the evolution of Brookfield viscosity at 100 rpm (in mPa.s) as a function of the quantity of 50% $CaCl_2$ solution.

EXAMPLE 15

Under the operating conditions of Example 12, viscosity measurements were effected in an aqueous suspension of mica, after 5 min of stirring, as a function of the quantity of C5 thinner. The mica tested is sold by the KAOLINS D'ARVOR company under the tradename MICARVOR 20; its particle size at 99.95% is less than 0.100 mm, at 99.9 less than 0.063 mm, and at 99.5% less than 0.040 mm.

Figure 7:
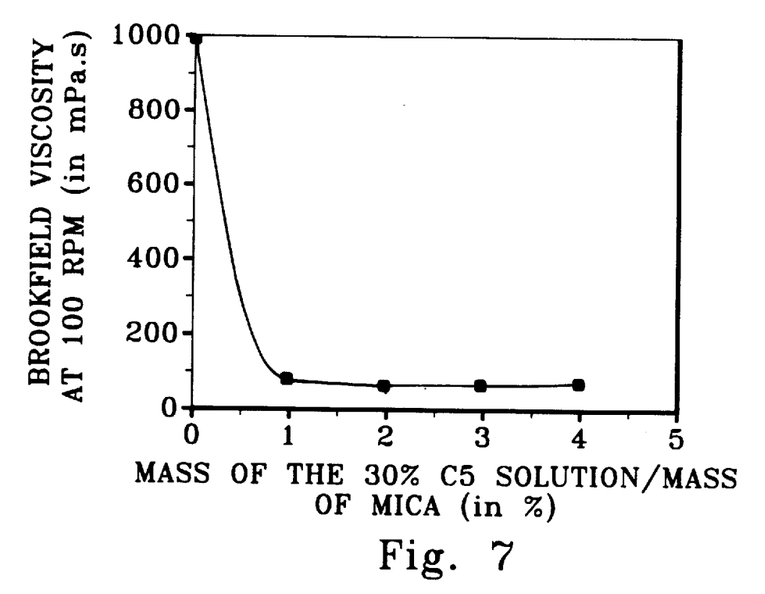
FIG. 7 is a graph of the evolution of viscosity of an aqueous suspension containing 200 g of mica, 133.3 g of water and variable quantities of C5 thinner, the water introduced with the thinner being subtracted to keep a constant water/mineral mass ration, as a function of the quantity of thinner introduced.

The suspensions tested contained 200 g of mica, 133.3 g of water and variable quantities of C5 thinner, the water introduced with the thinner being subtracted to keep a constant water/mineral mass ratio. FIG. 7 shows the evolution of viscosity (in mPa.s) as a function of the quantity of thinner introduced.

EXAMPLE 16

Under the operating conditions of Example 12, viscosity measurements were effected in an aqueous suspension of $TiO_2$, after 5 min of stirring, as a function of the quantity of C5 thinner. The $TiO_2$ tested is sold by the DEGUSSA company under the reference P25; the particle size is approximately 21 nm (nanometers) and their specific surface is approximately 50 $m^2/g$.

The aqueous suspensions tested contained 35% by weight $TiO_2$ before the first addition of thinner.

Figure 8:
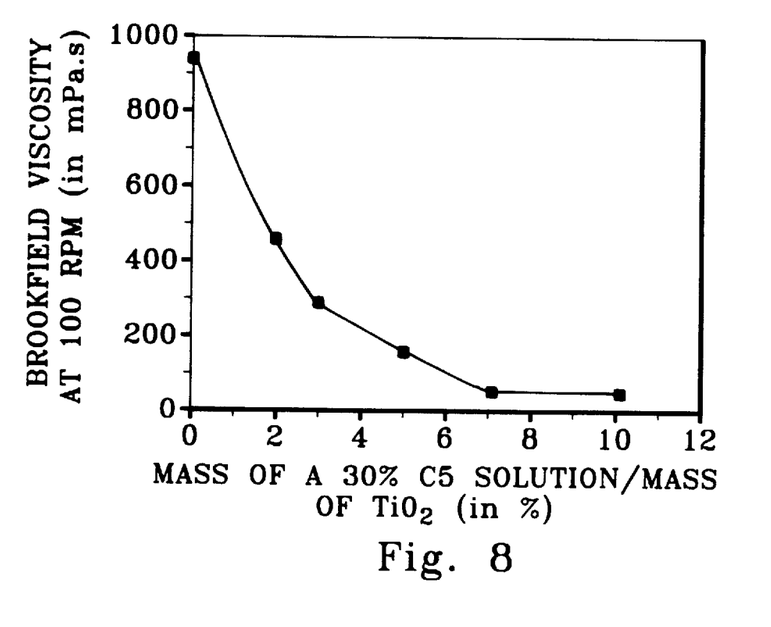
FIG. 8 is a graph of the evolution of viscosity of an aqueous suspension containing 35% by weight $TiO_2$ (before the addition of thinner), after 5 minutes of stirring, as a function of the quantity of C5 thinner added to the suspension.

FIG. 8 shows the evolution of the viscosity (in mPa.s) as a function of the quantity of thinner introduced.

EXAMPLE 17

This example illustrates the setting delay effect of certain compounds (I). This delay effect was measured on a standardized mortar (NF P-18356) placed in a truncated cone. After having leveled the surface of the cone filled with this mortar, the cone is placed in an automatic prisometer equipped with a needle and a mobile part according to standard NF P-15414. This test then consists of dropping the needle into the cone.

It is considered that:

the beginning of setting is realized as soon as the sinking of the needle is stopped at least 2.5 mm from the bottom of the cone, the end of setting is realized at the end of the time when the needle does not penetrate, for the first time, more than 2.5 mm below the leveled surface of the cone.

The products tested are described in Example 6.

| Products | Dosage (1) in % | Beginning of setting | End of setting |
|---|---|---|---|
| Control | 0 | 4 h 55 min | 9 h 06 min |
| C2 (diphosphonated n = 10) | 0.3 | 10 h 53 min | 22 h 19 min |
| C1 (monophosphonated n = 10) | 0.3 | 5 h 34 min | 10 h 45 min |
| Control | 0 | 5 h 05 min | 7 h 14 min |
| C2 | 0.375 | 21 h 43 min | more than 26 hours |
| C1 | 0.375 | 7 h 53 min | 10 h 55 min |
| Control | 0 | 4 h 20 min | 8 h 31 min |
| C4 (monophosphonated n = 100) | 0.3 | 6 h 22 min | 10 h 10 min |
| C5 (diphosphonated n = 100) | 0.3 | 7 h 30 | 11 h 57 |
| C3 (monophosphonated n = 50) | 0.3 | 5 h 44 min | 10 h 18 min |
| Control | 0 | 4 h 21 min | 9 h 18 min |
| C4 | 0.375 | 6 h 18 min | 12 h 01 min |
| C5 | 0.375 | 10 h 45 min | 12 h 52 min |
| C3 | 0.375 | 6 h 57 min | 9 h 29 min |

(1) The percentages are given in dry % with regard to the amount of cement.

EXAMPLE 18

In this example, a 30% aqueous solution (by weight with regard to the total weight of the solution) of compound C11 was used, whose purity was 85% and corresponding to the formula:

The aqueous solution defined above was introduced into concrete of composition:
- 900 kg of sand 0/5 of the silico-calcareous type
- 530 kg of gravel 5/15 of the silico-calcareous type
- 435 kg of granulate 15/25 of the silico-calcareous type
- 375 kg of CPA 55 PMES cement sold by the CIMENTS LAFARGE company in its Val d'Azergue factory, in an amount of 0.5% by mass of aqueous solution with regard to the concrete mass.

A thinning solution sold by the CHRYSO S. A. company under the trademark SUPERPLAST 760 (it comprises an aqueous solution based on polynaphthalene sulfonate) was also introduced into the same quantity of this concrete, in an amount of 0.5% by mass of Superplast solution with regard to the concrete mass.

The quantities of water introduced at t=0, defined by the water/concrete mass ratio (w/c) were adjusted so as to obtain identical fluidities (slumps) for the two concrete pastes upon arrival at the work site, or t=45 min.

The following table compiles the results of fluidity (slump) measurements:

|  | Concrete paste comprising 0.5% Superplast 760 solution | Concrete paste comprising 0.5% C11 compound solution |
|---|---|---|
| w/c | 0.43 | 0.39 |
| slump at t = 0 | 22 | 19 |
| slump at t = 45 | 19 | 18.5 |
| slump at t = 4 h (1) | 0(2) | 13.5 |

(1) slump measured after the concrete has remained for 4 hours in open air
(2) the concrete is solidified.

It appears therefore, on the one hand, that compound C11 permits obtaining a greater fluidity, which is translated by a water reduction of more than 9% (0.04/0.43) with regard to Superplast 760 and, on the other hand, that the fluidity conferred by compound C11 only slowly decreases over time.

Compressive strength measurements of concretes obtained after hardening were carried out according to standard NF P-18406.

|  | Concrete comprising Superplast 760 | Concrete comprising compound C11 | Improvement induced by C11 with regard to Superplast 760 |
|---|---|---|---|
| Strength at t = 7 days in mPa | 28.0 | 34.0 | +21.4% |
| Strength at t = 28 days in mPa | 33.5 | 41.0 | +22.4 |

It is observed that the strength at 7 days of a concrete comprising compound C11 of the invention is equal to, or even greater than, that of a concrete comprising Superplast 760 after 28 days of hardening.

EXAMPLE 19

In this example, the aqueous solution of compound C11 defined in Example 18 was introduced at t=0 into a first sample of mortar paste of composition:
- 300 g of aluminous cement sold by the CIMENTS LAFARGE company under the trademark LE FONDU
- 200 g of a slag sold by the English company "Civil & Marine"
- 1350 g of sand 0/5 of the silico-calcareous type
- 175 g of water in an amount of 0.5% by mass of aqueous solution with regard to the mass of the mortar.

In a second sample, composed of the same quantity of mortar paste defined above, at t=0, 1.5% of a commercial additive based on lignosulfonate sold under the tradename P7 by the CORMIX company was introduced.

In a third sample, composed of the same quantity of mortar paste defined above, at t=0, 1.5% of GT resin defined in Example 8 was introduced.

The fluidities of the mortars obtained, evaluated by means of spreading and measured in cm at the shock table according to the ASTM standard C86091 are indicated in the following table.

|  | t = 0 | t = 1 h 30 | t = 24 h |
|---|---|---|---|
| mortar comprising 1.5% commercial additive based on lignosulfonate | 97 | 69 | 40 |
| mortar comprising 1.5% GT resin | /(1) | /(1) | /(1) |
| mortar comprising 0.5% C11 solution. | 170 | 155 | 120 |

(1) The GT resin had only a fleeting thinning effect on the mortar, which was impossible to measure.

In a surprising manner, it is observed that the values of spreading are extremely high when an aqueous solution of compound C11 according to the invention is used.

Moreover, the fluidity of the mortar obtained with C11 decreases very little with time since at the end of 24 h, it is still 3 times greater than that of a mortar comprising the commercial thinner based on lignosulfonate.

Mechanical compressive strength measurements (expressed in mPa) according to standard NF EN 1961 and spreading measurements were effected on:
- the samples of mortar defined above (called reference mortar),
- and on mortar samples whose compositions were identical to that of the reference mortar, except for the water content, which is decreased.

The different mortars contained:
either 0.5% aqueous solution of compound C11
or 0.5% additive based on the lignosulfonate mentioned above in this example.

|  | Mortar containing 0.5% C11 solution | | Mortar containing 1.5% additive based on lignosulfonate | |
|---|---|---|---|---|
| Water content of the mortar in g | 175 (reference) | 160 | 150 | 175 (reference) |
| Compressive strength at t = 24 h | 28 | 32 | 34 | 23 |
| Spreading | 170 | 140 | 135 | 97 |

The compounds according to the invention therefore permit obtaining a fluidity greater than that generated by commercial thinners.

Consequently, at equal fluidity, a hydraulic binder paste containing a compound according to the invention will have the double advantage of having less water and less compound according to the invention, when compared with a hydraulic binder paste containing a commercial thinner.

This water reduction (when compared with hydraulic binder pastes containing a commercial thinner) has for an effect increasing the mechanical strength obtained after hardening.

EXAMPLE 20

The thinning capacity of compound C6, defined in Example 6, was evaluated by measuring the viscosity of suspensions of mineral particles S1, S2 and S3 containing 0.3% by weight of compound C6 with regard to the weight of mineral particles.

The S1 suspension contained alumina $Al_2O_3$ sold under the name P772SB by the Pechiney company and having a mass specific surface of 7.5 $m^2/g$.

The S2 suspension contained precipitated calcium fluoride $CaF_2$, sold by Prolabo and having a mass specific surface of 9 $m^2/g$.

The S3 suspension contained crushed silica $SiO_2$ sold by Sifraco under the trademark Sikron C800 and having a mass specific surface of 6 $m^2/g$.

The mass ratios (water/solid) of the quantity of water over the quantity of particles are given in the following table in which is also given the results of viscosity measurements effected by means of a measurement apparatus sold by the Contraves company under the name Rheomat 120.

|  | without thinner | | containing 0.3% C6 | |
|---|---|---|---|---|
| suspension | water/solid | viscosity (Pa.s) at 90 s − 1 | water/solid | viscosity (Pa.s) at 90 s − 1 |
| s1 | 0.57 | 1.0 | 0.21 | 0.7 |
| s2 | 0.50 | 2.1 | 0.30 | 1.9 |
| s3 | 0.58 | unmeasurable (1) | 0.45 | 7.0 |

(1) shearing threshold beyond the upper limits of the device.

The water reductions, defined as being the reduction in the water content generated by C6 when compared with a suspension not containing compound C6 and having the same viscosity, are more than 63% for S1, more than 40% for S2 and more than 22% for S3 (the percentages being expressed as a ratio to the viscosities of suspensions not containing compound C6).

We claim:

1. A process for fluidizing an aqueous suspension of mineral particles or hydraulic binder pastes which comprises admixing said aqueous suspension of mineral particles or hydraulic binder pastes with one or more compounds or salts of compounds corresponding to the general formula:

wherein:

R is a hydrogen atom or a saturated or unsaturated monovalent hydrocarbon group comprising 1 to 18 carbon atoms and optionally one or more heteroatoms;

$R_i$ is an alkylene or an arylene group optionally comprising one or more heteroatoms;

Q is a hydrocarbon group comprising 2 to 18 carbon atoms and optionally one or more heteroatoms;

A is an alkylidene group comprising 1 to 5 carbon atoms;

$R_j$ is selected from the group consisting of an $A\text{-}PO_3H_2$ group, an alkyl group comprising 1 to 18 carbon atoms and the group wherein $R_k$ is selected from the group consisting of an $A\text{-}PO_3H_2$ group and an alkyl group comprising 1 to 18 carbon atoms and B is an alkylene group comprising 2 to 18 carbon atoms;

n is 1 to 10,000;

r is the sum of $[R\text{-}O(R_i\text{-}O)_n]$ groups carried by all the $R_j$ groups;

q is the number of $[R\text{-}O(R_i\text{-}O)_n]$ groups carried by Q;

the sum r+q equals between 1 and 10;

y is a whole number ranging between 1 and 3;

Q, N and the $R_j$ groups optionally form together one or more rings, said ring or rings optionally comprising one or more heteroatoms;

the group $(R_i\text{-}O)_n$ can be the same or different when n>1; and, the group can be the same or different when y>1.

2. The process of claim 1 wherein R is selected from the group consisting of hydrogen, methyl, ethyl, nonylphenol and a hydrocarbon group comprising 12 to 18 carbon atoms.

3. The process of claim 2 wherein R is hydrogen.

4. The process of claim 1 wherein $R_i$ is selected from the group consisting of ethylene and propylene.

5. The process of claim 4 wherein $R_i$ is ethylene, the number of ethylene groups corresponding to $R_i$ being sufficient to conserve the water-soluble or water-dispersible character of the compounds of their salts.

6. The process of claim 1 wherein Q comprises 2 to 12 carbon atoms.

7. The process of claim 1 wherein A comprises 1 to 3 carbon atoms.

8. The process of claim 7 wherein A is methylene.

9. The process of claim 1 wherein $R_j$ is the $\text{-}CH_2\text{-}PO_3H_2$ group, or a salt thereof.

10. The process of claim 1 wherein $R_j$ is methyl.

11. The process of claim 1 wherein $R_j$ is the $C_2H_4N(CH2\text{-}PO_3H_2)_2$ group, or salt thereof.

12. The process of claim 1 wherein the salts are sodium, calcium or diethanolamine salts.

13. The process of claim 1 wherein n ranges between 1 and 500.

14. The process of claim 1 wherein n ranges between 1 and 250.

15. The process of claim 1 wherein the sum of r+q is less than 3.

16. The process of claim 1 wherein the sum of r+q is equal to 1.

17. The process of claim 1 wherein y is equal to 1.

18. The process of claim 1 wherein the mineral particles comprise mineral oxides.

19. The process of claim 1 wherein the mineral particles comprise calcium fillers or silicates.

20. The process of claim 1 wherein the hydraulic binder pastes are pastes of Portland cement, aluminous cements, α or β plaster, quicklime, pure phases of $3\ CaO.Al_2O_3$, $12CaO.7\ Al_2O_3$, $CaO.Al_2O_3$ and $2CaO.Al_2O_3$ cements or mixtures of these pastes.

* * * * *